(12) United States Patent
Ying et al.

(10) Patent No.: US 10,739,342 B2
(45) Date of Patent: Aug. 11, 2020

(54) TEST STRIP ASSEMBLY COMPRISING SAMPLE SORBENT STRIP, FLOW SEPARATOR, AND REAGENT SORBENT STRIP STACKED ON EACH OTHER

(71) Applicant: Agency For Science, Technology and Research, Singapore (SG)

(72) Inventors: Jackie Y. Ying, Singapore (SG); Yi Zhang, Singapore (SG); Jianhao Bai, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 469 days.

(21) Appl. No.: 15/507,206

(22) PCT Filed: Aug. 28, 2015

(86) PCT No.: PCT/SG2015/050286
§ 371 (c)(1),
(2) Date: Feb. 27, 2017

(87) PCT Pub. No.: WO2016/032402
PCT Pub. Date: Mar. 3, 2016

(65) Prior Publication Data
US 2017/0285022 A1    Oct. 5, 2017

(30) Foreign Application Priority Data
Aug. 29, 2014   (SG) ............................ 10201405333Q

(51) Int. Cl.
*G01N 33/558* (2006.01)
*G01N 33/543* (2006.01)
*G01N 33/52* (2006.01)

(52) U.S. Cl.
CPC ........... *G01N 33/558* (2013.01); *G01N 33/52* (2013.01); *G01N 33/543* (2013.01);
(Continued)

(58) Field of Classification Search
CPC ............. G01N 33/558; G01N 2333/02; G01N 2333/185; G01N 33/52; G01N 33/543; Y02A 50/53
See application file for complete search history.

(56) References Cited

U.S. PATENT DOCUMENTS 4,960,691 A    10/1990   Gordon et al.
5,736,188 A     4/1998   Alcock et al.
(Continued)

FOREIGN PATENT DOCUMENTS

WO    WO-01/81915 A1     11/2001
WO    WO-2014/085926 A1   6/2014

OTHER PUBLICATIONS

International Search Report for PCT/SG2015/050286, 6 pages (dated Oct. 23, 2015).
(Continued)

*Primary Examiner* — Tracy Vivlemore
*Assistant Examiner* — Nam P Nguyen
(74) *Attorney, Agent, or Firm* — Choate, Hall & Stewart LLP; Brian E. Reese; Dana M. Daukss

(57) ABSTRACT

There is provided a test strip assembly for detecting the possible presence of at least one analyte in a sample, a device for detecting the possible presence of at least one analyte in a sample comprising the test strip assembly and methods of detecting the possible presence of at least one analyte in a sample using the device.

20 Claims, 7 Drawing Sheets

(52) U.S. Cl.
   CPC ... *G01N 2333/02* (2013.01); *G01N 2333/185* (2013.01); *Y02A 50/53* (2018.01)

(56) References Cited

U.S. PATENT DOCUMENTS

| | | | | |
|---|---|---|---|---|
| 5,837,546 A | * | 11/1998 | Allen | G01N 21/8483 436/169 |
| 5,968,839 A | * | 10/1999 | Blatt | G01N 33/558 435/11 |
| 8,603,835 B2 | | 12/2013 | Esfandiari | |
| 2002/0006670 A1 | | 1/2002 | Wu et al. | |
| 2003/0103869 A1 | * | 6/2003 | Hardman | B01L 3/5023 436/518 |
| 2004/0029177 A1 | * | 2/2004 | Nadaoka | G01N 33/558 435/7.1 |
| 2005/0266499 A1 | | 12/2005 | Tan et al. | |
| 2008/0213133 A1 | | 9/2008 | Wallace et al. | |
| 2008/0318341 A1 | | 12/2008 | Esfandiari | |
| 2011/0091870 A1 | * | 4/2011 | Lang | G01N 33/54393 435/6.11 |
| 2012/0288961 A1 | * | 11/2012 | Yager | B01L 3/5023 436/501 |
| 2013/0164734 A1 | | 6/2013 | Raychaudhuri et al. | |
| 2014/0370502 A1 | * | 12/2014 | Brennan | G01N 33/54386 435/6.11 |

OTHER PUBLICATIONS

Written Opinion for PCT/SG2015/050286, 5 pages (dated Oct. 23, 2015).

Tanaka, R. et al., A novel enhancement assay for immunochromatographic test strips using gold nanoparticles, Anal Bioanal Chem, 385: 1414-1420 (2006).

* cited by examiner a b a b c

TEST STRIP ASSEMBLY COMPRISING SAMPLE SORBENT STRIP, FLOW SEPARATOR, AND REAGENT SORBENT STRIP STACKED ON EACH OTHER

CROSS-REFERENCE TO RELATED APPLICATIONS

This patent application is a National Stage Entry of International Patent Application No. PCT/SG2015/050286, filed on Aug. 28, 2015 which claims the benefit of priority of Singapore application no. 10201405333Q, filed Aug. 29, 2014, the contents of each of which are hereby incorporated by reference in their entirety for all purposes herein.

TECHNICAL FIELD

The present invention relates to the field of biochemistry, in particular devices for detection of biochemical molecules.

BACKGROUND ART

A wide variety of ligand-receptor assays have been used to detect the presence of targets of interest in bodily fluids, such as serum, urine or saliva. These assays generally involve the capture and tagging of the target of interest on a solid substrate through antibody-antigen interactions, followed by signal generation with enzymatic, colorimetric, fluorescent or radioactive conjugates. These tests are relatively inexpensive, reliable, and easy to conduct. However, the sensitivity of lateral flow assays is frequently compromised by the formation of aggregates between conjugates and samples that prevent the labeled analytes from reaching the test zone for detection. Furthermore, the sensitivity of lateral flow assays is reduced when there is excess liquid, which floods the test strip and leads to insufficient reaction. The two issues mentioned above are particularly evident when dealing with samples containing salivary fluid.

However, unlike the other fluid specimens, salivary fluid cannot be applied directly to commercially available blood or urine lateral flow test strips because saliva samples do not flow easily. Further, saliva samples cause the detector colloidal particles to non-specifically adhere to the nitrocellulose membrane, thereby causing false results. This peculiar behavior is believed to be due to the presence of high concentrations of mucin and other highly viscous substances in the salivary fluid. Despite of its easy accessibility, salivary fluid usually contains very small amount of immunoglobulins. Compared to serum, the IgG and IgM levels in saliva are lower by a few orders of magnitude. Therefore, in order to obtain accurate results, a large volume of saliva sample is required for each test. However, conventional lateral flow devices are often not designed to handle large sample volumes. If too much sample is applied, it will result in overflow of the fluid and cause flooding of the test strip, bringing about disadvantages as discussed above.

Further, in most existing saliva-based tests, samples are collected and processed separately before being introduced to the assay. The salivary fluid is either collected in liquid form by drooling into containers, sometimes with the assistance of capillary tubes and pipettes, or collected on a solid substrate by chewing on paraffin, foam, cotton swab or other liquid-absorbent materials. Samples collected in liquid form are then centrifuged to remove the cellular components in order to obtain the saliva supernatant. Samples collected on solid substrates are usually eluted in buffers that are compatible with the subsequent assay desired. Samples collected on solid substrates may also be released into containers by pressurizing the solid materials. Such complicated sample collection and pretreatment procedures reduce the applicability of the salivary fluidics in lateral flow tests. Further, in one case, the saliva samples require a separate preparation step before they can be introduced to the lateral flow device. In another case, saliva samples can be collected with an integrated device, but no sample treatment step is demonstrated, hence it is not suitable for lateral flow-based saliva analysis. In yet another case, the saliva sample can be directly introduced to the lateral flow device, and an in-line sample pretreatment method is available to bridge the raw saliva sample to the lateral flow test strip, but the device is not able to process large sample volume, and the use of mucolytic agents may interfere with the lateral flow assay. In still another case, salivary fluid is collected onto a sorbent pad by swabbing the gum. The sample-carrying pad, which is directly coupled to the test strip, is subsequently submerged in the desired buffer to allow reactions to occur. However, the test strip does not assist in the flow of the sample as the sample has to flow against gravity. In yet another case, samples and reagents have to be introduced into a lateral flow assay separately, after one has completely migrated to the test zone, and the contact point of the sample and reagent at the test zone cannot be controlled or altered, resulting in inflexibility. Some designs of lateral flow devices may also not be streamlined, thereby resulting in difficulty of handling.

Accordingly, there is a need to provide alternative devices to analyze samples.

SUMMARY OF INVENTION

In a first aspect, there is provided a test strip assembly for detecting the possible presence of at least one analyte in a sample, comprising: a test strip for immobilizing at least one capture agent and detecting the analyte, if present, at a test site on the test strip; a sample sorbent strip having a first location for receiving the sample and a connecting portion for connecting the first location with a second location, the connecting portion defining a sample flow path to the second location; a reagent sorbent strip having a first location for receiving a reaction reagent for analyte detection reaction and a connecting portion for connecting the first location with a second location, the connecting portion defining a reagent flow path to the second location; wherein at least a portion of the test strip, the second location of the sample sorbent strip and the second location of the reagent sorbent strip intersect with each other at an intersection, wherein the second location of the sample sorbent strip and the second location of the reagent sorbent strip each form at the intersection a flow path directing the sample flow path and the reagent flow path towards the test strip in substantially the same direction, wherein the sample sorbent strip and the reagent sorbent strip contact the test strip at the same or at separate locations.

In a second aspect, there is provided a device for detecting the possible presence of at least one analyte in a sample, comprising: the test strip assembly as disclosed herein; a housing comprising a top piece and a bottom piece, the housing configurable to enclose the test strip assembly.

In a third aspect, there is provided a method of detecting the possible presence of at least one analyte in a sample using the device as disclosed herein, comprising: introducing the sample into the sample inlet to allow the sample sorbent strip to absorb the sample; introducing the reaction reagent into the reagent inlet to allow the reagent sorbent strip to absorb the reaction reagent; reading a signal generated on the test strip at the test site indicating the presence or absence of the at least one analyte.

In a fourth aspect, there is provided a method of detecting the possible presence of at least one target analyte in a sample by using the device as disclosed herein.

BRIEF DESCRIPTION OF DRAWINGS

The invention will be better understood with reference to the detailed description when considered in conjunction with the non-limiting examples and the accompanying drawings, in which:

FIG. 4 is an illustration of a test strip assembly 120 comprising two sorbent strips according to an embodiment of the present invention in a) collapsed view, b) exploded view, c) top view, and d) cross sectional view, while FIG. 4e is an illustration of the flow direction of the two sorbent strips to the test strip 124.

FIG. 5aii shows the dye signal in the test zone of the test strip along test line A-A'.

DETAILED DESCRIPTION

Figure 1:
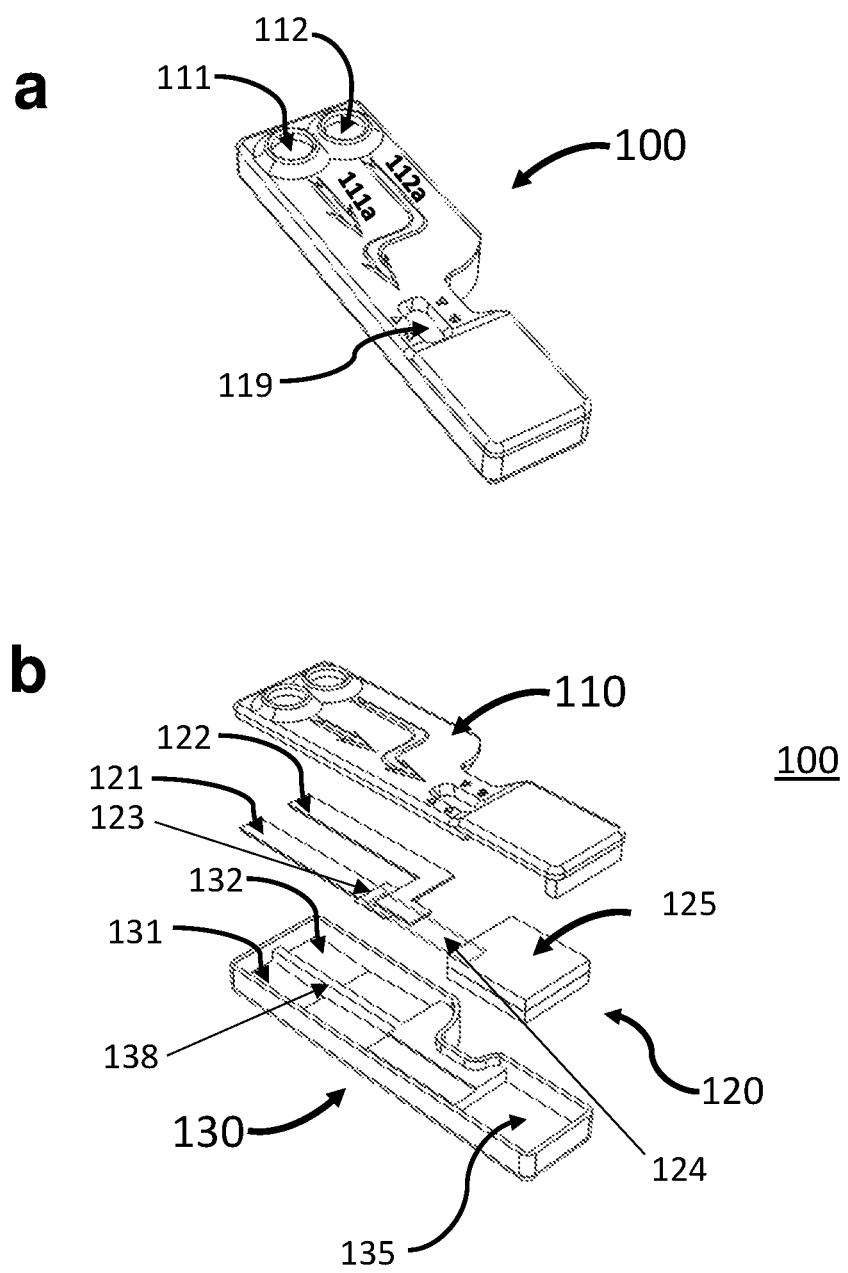
FIG. 1 is an illustration of a device 100 comprising top piece 110, test strip assembly 120 and bottom piece 130 according to an embodiment of the present invention in a) collapsed view and b) exploded view.

Lateral flow immunoassays generally involve the capture and tagging of a target of interest with antigens or antibodies immobilized on a test zone of sorbent materials. Typically, in these assays, samples that may comprise the target of interest and reagents that generate signals upon reaction are introduced onto sorbent material, and are allowed to wick by capillary force to a test zone where antigens or antibodies are immobilized. As the sample flows through the sorbent material, the target of interest or analyte binds to the immobilized antigens or antibodies. The binding of the target of interest generates a signal and results in visually distinguishable lines or spots in the test zone.

In a first aspect, the present invention refers to a test strip assembly for detecting the possible presence of at least one analyte in a sample. The test strip assembly may comprise a test strip for immobilizing at least one capture agent and detecting the analyte, if present, at a test site on the test strip. The test strip assembly may comprise a sample sorbent strip having a first location for receiving the sample and a connecting portion for connecting the first location with a second location, the connecting portion defining a sample flow path to the second location. The test strip assembly may comprise a reagent sorbent strip having a first location for receiving a reaction reagent for analyte detection reaction and a connecting portion for connecting the first location with a second location, the connecting portion defining a reagent flow path to the second location. At least a portion of the test strip, the second location of the sample sorbent strip and the second location of the reagent sorbent strip may intersect with each other at an intersection. The second location of the sample sorbent strip and the second location of the reagent sorbent strip each may form, at the intersection, a flow path directing the sample flow path and the reagent flow path towards the test strip in substantially the same direction. The sample sorbent strip and the reagent sorbent strip may contact the test strip at the same or at separate locations.

The sample flow path and the reagent flow path may run in substantially the same direction at the intersection. The sample sorbent strip and reagent sorbent strip may intersect with the test strip in such a manner that all fluids guided by the sorbent strips enter the test strip in substantially the same direction. Advantageously, uniform flow of the fluids may be achieved when multiple streams migrate concurrently to the test strip in substantially the same direction.

In an example, the sample flow path may be substantially parallel to the reagent flow path in the same vertical plane at the intersection. The sample flow path may run above the reagent flow path in substantially the same direction at the intersection. The reagent flow path may run above the sample flow path in substantially the same direction at the intersection. That is, the second location of the sample sorbent strip may be above the second location of the reagent sorbent strip in the same vertical plane, or the second location of the reagent sorbent strip may be above the second location of the sample sorbent strip in the same vertical plane. The second location of the sample sorbent strip and the second location of the reagent sorbent strip may be stacked on each other at the intersection. To contact the test strip, the second locations of the sorbent strips may bend and lie over the test strip, or the connecting portions of the sorbent strips may bend to enable the second locations to lie over the test strip. Advantageously, the arrangement enables the disclosed test strip assembly to be compact. Advantageously, the arrangement enables the reduction in footprint of a test strip assembly, reducing the amount of space taken up by the test strip assembly.

In another example, the sample flow path may be substantially parallel to the reagent flow path in the same horizontal plane at the intersection. The sample flow path may run alongside the reagent flow path at the intersection. That is, the second location of the sample sorbent strip may be beside or adjacent to the second location of the reagent sorbent strip in the same horizontal plane.

In yet other examples, the sample flow path may be substantially parallel to the reagent flow path in a plane offset from the horizontal plane at the intersection. The second location of the sample sorbent strip may be beside the second location of the reagent sorbent strip but at a higher vertical level. The second location of the reagent sorbent strip may be beside the second location of the sample sorbent strip but at a higher vertical level. The second location of the sample sorbent strip may be stacked diagonally on the second location of the reagent sorbent strip. The second location of the reagent sorbent strip may be stacked diagonally on the second location of the sample sorbent strip.

Advantageously, due to the arrangement of the flow paths to be in substantially the same direction at the intersection, substantially uniform flow rates may be achieved when the flow paths intersect at the intersection. Advantageously, the sample and reagent may be controlled to migrate concurrently to the test strip with uniform flow. Advantageously, the uniformity of liquid flow through the test site may be greatly improved.

The term "substantially" when used with "same direction" is to be interpreted broadly to refer to a flow path flowing in the same general direction. The term "substantially" in the context of parallel flow paths at the intersection is to be interpreted in the same way. Where the flow paths of multiple liquids intersect at an area slightly larger than the area of the combined flow paths, i.e. when the intersection area is relatively small, the flow paths of the multiple liquids have to be maintained in the same direction to stay within the intersection area. On the other hand, where the flow paths of multiple liquids intersect at an area much larger than the area of the combined flow paths, i.e. when the intersection area is relatively large, the flow paths of the multiple liquids have larger freedom to flow and need only to flow in the same general direction.

The sample sorbent strip may contact the test strip at any location depending on the requirement of the assay. The reagent sorbent strip may contact the test strip at any location depending on the requirement of the assay. For example, the sample sorbent strip may advantageously contact the test strip near or at the test site if interaction of the sample and the test strip is to be minimized. In another example, the sample sorbent strip may contact the test strip further away from the test site if a plurality of sample sorbent strips and/or a plurality of reagent sorbent strips are provided. Further advantageously, the reaction time between an analyte in the sample and the reagent may be adjusted by controlling the distance between the intersection and the test site. For example, if the analyte requires a longer time to react with the reagent, the intersection may be located at a position further away from the test site.

The sample sorbent strip may contact the test strip at the same or at a different location as the reagent sorbent strip, depending on the requirement of the assay. Advantageously, flow paths may be free to enter the test strip at arbitrary locations as required. Advantageously, the position and timing of contact between the sample and reagent can be controlled. For example, if a reaction between an analyte in the sample and the reagent is not desired before the capture of the analyte at the test site, one of the sorbent strips, e.g. the reagent sorbent strip, may be configured to contact the test strip at a position closer to the test site than where the other strip contacts the test strip.

An edge or edge portion of at least one of the sorbent strips may be arranged to contact an edge or an edge portion of the test strip. The edge portion may be a section of the strip close to the edge. The sample or reagent may be urged by the pressure of the flow and/or the concentration difference towards the opposite edge of the test strip and therefore, towards the test site. Advantageously, as the sample or reagent flows from the sorbent strip to the test strip and contact the test strip at one end, the sample or reagent may diffuse in a direction away from the end and toward the opposite end, toward the test site. While diffusion of sample or reagent may occur in all directions, the diffusion of sample or reagent away from the test site may be negligible due to the momentum of the flow. Advantageously, backflow of sample or reagent on the test strip may be prevented. FIG. 4e shows an illustration of a sample (through the sample sorbent strip) contacting the test strip at an edge portion and flowing towards the test site. FIG. 4e also shows the reagent (through the reagent sorbent strip) contacting the test strip at a location nearer the test site as compared to the sample sorbent strip. The sample flowing through the test strip in the direction of the test site contacts the reagent at the intersection. The pressure of the sample flow causes the reagent to flow in the same direction towards the test site.

The first location of the sample sorbent strip and the first location of the reagent sorbent strip may be arranged substantially parallel to each other. The connecting portion of the sample sorbent strip and the connecting portion of the reagent sorbent strip may be arranged substantially parallel to each other. The first location and connecting portion of the sample sorbent strip and the first location and connecting portion of the reagent sorbent strip may be arranged substantially parallel to each other. Advantageously, the parallel arrangement provides a streamline configuration of the test strip assembly and significantly reduces the footprint compared to T-shaped, Y-shaped, or cross-shaped arrangements between the sample, reagent and test strips. However, depending on the application, the arrangement of the sorbent strips may include non-parallel configurations and T-shaped, Y-shaped, or cross-shaped arrangements of sorbent strips are not excluded.

The first location and/or connecting portion of the sample sorbent strip and the first location and/or connecting portion of the reagent sorbent strip may be arranged above, stacked or substantially parallel to each other in the same vertical plane. The first location and/or connecting portion of the sample sorbent strip and the first location and/or connecting portion of the reagent sorbent strip may be arranged beside or substantially parallel to each other in the same horizontal plane. The first location and/or connecting portion of the sample sorbent strip and the first location and/or connecting portion of the reagent sorbent strip may be arranged diagonally above or substantially parallel to each other in a plane offset from the horizontal plane.

The term "substantially parallel" in the context of sections of strips is to be interpreted broadly to refer to adjacent sections arranged in generally the same orientation.

The sample sorbent strip and the reagent sorbent strip may be: (i) in the same horizontal plane as the test strip; (ii) in a plane perpendicular to the plane of the test strip or in the same vertical plane as the test strip; or (iii) in a plane offset to the plane of the test strip.

To contact the test strip, the second locations of the sorbent strips may bend downwards or diagonally downwards or perpendicularly and lie over the test strip. Alternatively, the connecting portions of the sorbent strips may bend downwards or diagonally downwards or perpendicularly to enable the second locations to lie over the test strip. The second locations or connecting portions of the sorbent strips may be bent to contact the test strip by pressure exerted by biasing means.

The disclosed test strip assembly may comprise a flow separator to prevent the sample flow path and the reagent flow path from mixing before reaching the test strip. Advantageously, the sample and the reagent are prevented from undesired reaction before reaching the test strip. Further advantageously, backflow of the sample or reagent, e.g. to the reagent sorbent strip or sample sorbent strip, respectively, may be prevented.

In one example, the connecting portion of the sample sorbent strip and the connecting portion of the reagent sorbent strip may be stacked on each other. In another example, the connecting portion of the sample sorbent strip may be adjacent and abut the connecting portion of the reagent sorbent strip in the same horizontal plane. In yet other examples, the connecting portion of the sample sorbent strip may be diagonally above and contacting a length of the connecting portion of the reagent sorbent strip. In yet other examples, the connecting portion of the reagent sorbent strip may be diagonally above and contacting a length of the connecting portion of the sample sorbent strip. In these examples, the flow separator may be suitably arranged between the connecting portions to prevent the connecting portions from directly contacting each other, thereby preventing the sample flow path and the reagent flow path from mixing prematurely.

In examples where a substantial length of the sample sorbent strip (e.g. from the first location to the second location) and a substantial length of the reagent sorbent strip are stacked on each other, or where a substantial length of the sample sorbent strip is adjacent and abut a substantial length of the reagent sorbent strip in the same horizontal plane, or where a substantial length of the sample sorbent strip is diagonally above and contacting a substantial length of the reagent sorbent strip, or where a substantial length of the reagent sorbent strip is diagonally above and contacting a substantial length of the sample sorbent strip, the flow separator may be suitably arranged between the substantial lengths to prevent the sample sorbent strip and reagent sorbent strip from directly contacting each other, thereby preventing the sample flow path and the reagent flow path from mixing prematurely.

In examples where the sample sorbent strip and the reagent sorbent strip intersect each other at the intersection, the flow separator may be suitably arranged between the second locations to prevent the sample and reagent from mixing before reaching the test strip. The flow separator may be located between the second location of the sample sorbent strip and the second location of the reagent sorbent strip to prevent the flow path at the intersection from mixing before reaching the test strip. The sample flow path and the reagent flow path may thus advantageously be prevented from crossing each other before reaching the test strip.

In the example where the second location of the sample sorbent strip is above or stacked on the second location of the reagent sorbent strip in the same vertical plane, or in a plane offset from the horizontal plane, or where the second location of the reagent sorbent strip is above or stacked on the second location of the sample sorbent strip in the same vertical plane, or in a plane offset from the horizontal plane, the flow separator may be located therebetween. The flow separator advantageously enables the strips to be stacked without compromising effectiveness of the assay.

The flow separator may be sized to allow the sample sorbent strip and the reagent sorbent strip to contact the test strip across substantially the entire width of the test strip. Advantageously, in examples where the flow separator is between at least a portion of adjacent sorbent strips, the flow separator may be arranged to guide and direct the sample and the reagent to contact the test strip across substantially its entire width. Advantageously, the flow separator may prevent the sample and reagent from deviating from the original flow path along the respective sorbent strip and thereby contact the test strip only at the desired location or area. Advantageously, when sample and reagent are concurrently introduced, the flow separator may guide the sample and reagent to enter the test strip in substantially the same direction in order to achieve uniform flow.

The sample sorbent strip and the reagent sorbent strip may be arranged to contact the test strip across substantially the entire width of the test strip so that the sample and reagent contact the test strip across substantially the entire width of the test strip. In an example, the flow separator has the same width or a larger width as the sample sorbent strip and the reagent sorbent strip. Advantageously, uniform flow of the sample and reagent in the test strip may be achieved. Advantageously, the sample or reagent may not leak onto the test strip at an undesired location, such as at an edge of the test strip, and result in non-uniform flow in the test strip.

The disclosed test strip assembly may further comprise more than one sample sorbent strip. The disclosed test strip assembly may further comprise more than one reagent sorbent strip. Advantageously, the assembly may be able to accommodate two or more flow paths as necessary. Advantageously, multiple sample sorbent strips and reagent sorbent strips can be included for more complex assay formats.

The plurality of sample sorbent strips and/or the plurality of reagent sorbent strips may be arranged relative to each other as disclosed herein. For example, one sample sorbent strip may be provided with two reagent sorbent strips and arranged in between the reagent sorbent strips in the same vertical plane or in the same horizontal plane. In another example, the second location of one sample sorbent strip is arranged in between the second locations of two reagent sorbent strips at the intersection. In other examples, the second locations of the sorbent strips are stacked on each other at the intersection. Flow separators may be provided in between adjacent sorbent strips in arrangements as disclosed herein. In an example, flow separators are located between the second locations of adjacent sorbent strips to prevent the flow path at the intersection from mixing before reaching the test strip. In another example, each flow separator is located between two sorbent strips at the intersection. The number of sample and reagent sorbent strips may be varied as required by the assay. For example, multiplexed assays require more than one analyte to be detected and therefore, a test strip assembly for such an assay may comprise more than one sample sorbent strip. Advantageously, the disclose test strip assembly may provide multiple flow paths, each of which carries distinct samples or reagents. Further advantageously, due to the configuration of the test strip assembly as disclosed herein, liquids in all flow paths can migrate concurrently (or separately as required by the assay) and enter the test strip in the same direction and thereby result in uniform flow in the test strip.

In a particular example, a plurality of sample sorbent strips and reagent sorbent strips may be stacked over one another, with flow separators provided in between adjacent sorbent strips, at the intersection with the test strip.

The flow separator may be made of a material that is impermeable to the sample and the reagent. "Impermeable" means that a sample or reagent comprised in the sorbent strip does not pass through the flow separator to the adjacent sorbent strip. The flow separator may be a layer of liquid-impermeable thin film. Where the flow separator is arranged between portions of adjacent sorbent strips, the flow separator may additionally comprise a material sufficiently flexible to bend in tandem with the sorbent strips. The flow separator may comprise a material that is either rigid or flexible. The flow separator may comprise a flexible material that is made rigid. The flow separator may be cut into a desired shape and/or dimension by any suitable means, such as a laser cutter optionally controlled by a computer or a stylus cutter. The flow separator may comprise glass, metals, metal foils (e.g. aluminum, copper), polymers (e.g. polystyrene, polyolefin, polycarbonate), rubber, ceramics or combinations thereof. The flow separator may comprise an optional adhesive coating to ensure that the flow separator is maintained in place.

The sample may be a fluid sample. The sample may be a liquid sample, for example bodily fluids such as blood, urine, serum, saliva, sputum, or other bodily fluids. The sample may be industrial fluids, for example pharmaceutical solutions for testing of contamination.

In an example, the sample is a saliva sample. Advantageously, salivary fluid is an important source of biomarkers, and is useful for rapid point-of-care diagnostics. The immunoglobulins (e.g. IgGs and IgMs) found in salivary fluid are directly related to those in blood. Human saliva also carries lymphocytes and plasma cells, which may also serve as biomarkers. Certain immunoglobulins, such as secretory IgA, are found in large quantities in saliva. Further, steroids passively carried into saliva closely correlate to the quantities in plasma. In addition, salivary fluid can be easily collected in a non-invasive manner, leading to higher patients' compliance and willingness. Accordingly, the use of salivary fluid as the sample may provide a simple and easy way of assessing the presence of markers that serve as indications of oral and systemic diseases.

The properties of each sorbent strip may be chosen to control the permeation of the liquid, sample or reagent, thereby controlling the travel times between the respective first locations and the test strip. The properties of each sorbent strip may be chosen to allow different travel times between the respective first locations and the test strip.

The property of the sorbent strip may be selected from one or more or all of the group consisting of but not limited to: pore size, porosity, bed volume and wicking rate.

An example of the pore size of the sorbent strip may be from about 1 nm to about 1 mm, or about 100 nm, or about 500 nm, or about 1 μm, or about 500 μm. An example of the bed volume of the sorbent strip may be 1 μL/cm to 1 mL/cm, or about 10 μL/cm, or about 100 μL/cm, or about 500 μL/cm. An example of the wicking rate of the sorbent strip may be about 30 seconds to 30 minutes, or about 1 minute, or about 10 minutes, or about 20 minutes. It will be apparent that other examples may be possible depending on the requirements of the assay.

The sample sorbent strip may be comprised of a material suitable to filter out unwanted components from the sample while being conveyed to the test strip by capillary force. For example, the sample sorbent strip may be capable of filtering out cellular debris and other solid contaminants from salivary fluid as it permeates through the sample sorbent strip towards the test strip. Advantageously, the sample may be pre-treated in the sample sorbent strip prior to reaction, thereby addressing the aforementioned issues associated with using salivary fluid and other types of body fluid as a medium for the analysis of targets of interest. Advantageously, the disclosed test strip assembly may not require additional pretreatment for biological fluids prior to use and may thus be simple to use.

The reagent sorbent strip may be comprised of a material suitable to receive a reaction reagent for analyte detection reaction. The reaction reagent may be in liquid form. The reaction reagent may be a dry reagent immobilized onto the reagent sorbent strip, including the first location of the reagent sorbent strip. The dry reagent may be dehydrated on the reagent sorbent strip, including the first location of the reagent sorbent strip. The reagent sorbent strip may comprise a detection agent immobilized thereon. The reagent sorbent strip may comprise preservatives to protect the reagent dehydrated thereon.

The reagent sorbent strip may comprise a material that is the same or different from the sample sorbent strip. The flow rate of the sample through the sample sorbent strip may advantageously be varied relative to the flow rate of the reagent through the reagent sorbent strip, thereby providing control of the respective flow rates.

The sorbent strip may comprise sorbent materials of various types. The sorbent strip may comprise a material sufficiently flexible to bend or fold, e.g. to contact the test strip. The sorbent strip may comprise inorganic or organic porous materials, including glass fiber, cellulose, cellulose acetate, nitrocellulose, other porous polymers and combinations thereof. The material of each sorbent strip may be selected from the group consisting of glass fiber, cellulose, cellulose acetate and a combination thereof.

The test strip may be made of a material capable of binding protein, such as membranes made of nitrocellulose, cellulose, cellulose acetate and nylon. The test strip may be made of a material having a high protein binding capacity.

The thickness and/or length of each sorbent strip may be chosen to allow different travel times between the respective first locations and the test strip.

An exemplary thickness of each sorbent strip may range from about 20 μm to about 200 μm, or about 50 μm, or about 100 μm, or about 150 μm. An exemplary length of each sorbent strip may range from about 2 cm to about 10 cm, or about 5 cm. It will be apparent that other exemplary dimensions may be possible depending on the requirements of the assay.

The test strip assembly may further comprise a waste sorbent pad located downstream of the test site for collecting waste reagents and/or samples that pass through the test strip. The waste sorbent pad may collect all the waste materials downstream the test site.

At least one, or two, or three, or more capture agents may be immobilized at the test site, which may be located along the length of the test strip at a point after the sample flow and the reagent flow contact the test strip. In an example, ten capture agents may be immobilized at the test site, and ten analytes may be detected.

In a second aspect, the present invention refers to a device for detecting the possible presence of at least one analyte in a sample. The device may comprise the test strip assembly as disclosed herein. The device may comprise a housing comprising a top piece and a bottom piece, the housing configurable to enclose the test strip assembly.

The device may be compact, may have a streamline configuration and may be easy to use as described herein.

The top piece may comprise a sample inlet located above the first location of each sample sorbent strip, and a reagent inlet located above the first location of each reagent sorbent strip. The sample inlet and reagent inlet may be constructed as known in the art. The sample inlet and reagent inlet may be openings sized suitably for receiving sample and reaction reagent, respectively.

The bottom piece may comprise a sample chamber located below the first location of each sample sorbent strip, and a reagent chamber located below the first location of each reagent sorbent strip.

The chambers may be sized to house substantial lengths of the respective strips. At least a portion of the sample sorbent strip may be housed within or extend into the sample chamber. At least a portion of the reagent sorbent strip may be housed within or extend into the reagent chamber. Sample or reagent may be introduced into the inlets, contact the first locations and wick through the sorbent strips to migrate towards the test strip.

The chamber may be an elongate depression corresponding to the length of the strip. The chambers may be separate chambers separated from each other by a dividing wall between adjacent chambers. The chambers may be a single chamber having designated areas to house the various parts of the test strip assembly. The chambers may be partially separated chambers separated from each other by a dividing wall between adjacent chambers, wherein the dividing wall does not extend to the entire height of the device.

The bottom piece may comprise a test chamber to house the test strip. The test chamber may be shallower than the sample chamber and reagent chamber to prevent the test strip from being submerged into the excess sample or reagent in the chambers. The depths of the chambers may be varied gradually. The sample and reagent chambers may gradually slope toward the test chamber. The depths of the chambers may be varied by steps.

Advantageously, the chambers are sized to contain large volumes of liquid, to thereby prevent flooding of the test strip when large volumes of sample or reagent are introduced. Advantageously, the sample chamber and the reagent chamber may have volumes sufficient to prevent flooding of the test strip due to large liquid volume. Advantageously, the device may be able to handle a wide range of sample and reagent volumes. Advantageously, the reaction at the test site may be sufficient to provide detection of the analyte even though large volumes of liquid are introduced. Advantageously, the sensitivity of the disclosed device may be improved as compared to prior art devices resulting from since flooding is prevented. In an example, the chamber may be able to contain about 5 mL of liquid. In other examples, the chamber may be able to contain less than about 5 mL of liquid, or about 3 mL of liquid, or about 1 mL of liquid.

The chambers may be sized to handle minimal volumes of liquid and yet yield reactions sufficient to provide detection of the analyte. In an example, a liquid volume of about 1 μL, or about 5 μL, or about 10 μL, may be sufficient to provide detection of the analyte.

The bottom piece may comprise more than one sample chamber and/or more than one reagent chamber corresponding with the number of sorbent strips provided in the test strip assembly.

The bottom piece may comprise a waste chamber located below the waste sorbent pad. Materials remaining after reaction at the test site may be absorbed by the waste sorbent pad or collected in the waste chamber to further prevent flooding. The waste chamber may collect all the waste materials downstream of the test site.

The chambers may be capable of containing milliliters of liquid.

The top piece may further comprise biasing means to bias the sorbent strips into their respective chambers. The biasing means may not prevent the permeation of sample or reagent through the sorbent strips.

The top piece may comprise one or more observation windows located above the test site. Advantageously, the observation windows allow visualization of the test site upon completion of the reaction.

FIGS. 1, 2, 4, 6 and 7 show devices according to embodiments as disclosed herein, wherein like numerals denote like parts, as will be explained below.

Figure 7:
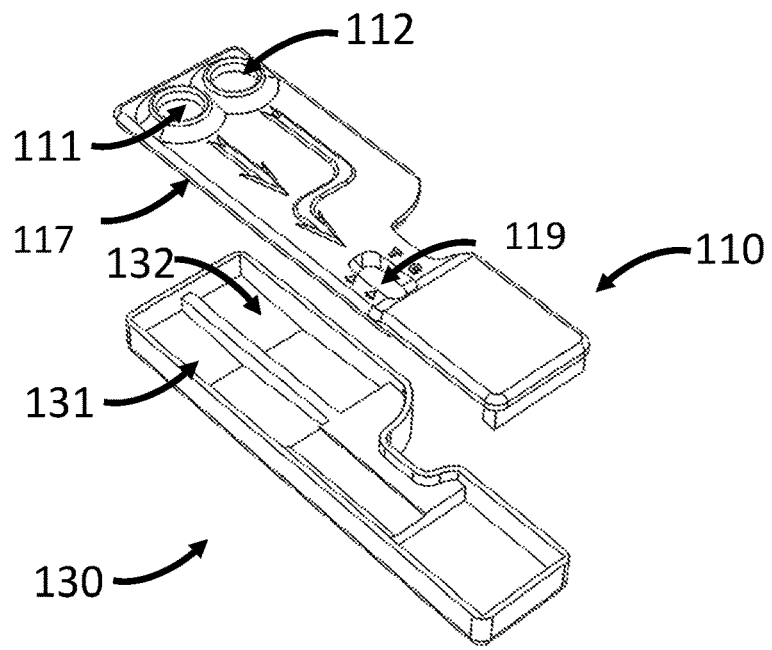
FIG. 7 is an illustration of top piece 110 and bottom piece 130 of a device according to an embodiment of the present invention in exploded view.

A device 100 according to an embodiment as disclosed herein is illustrated in FIG. 1 in collapsed view (FIG. 1a) and exploded view (FIG. 1b). The device 100 includes a test strip assembly 120 and a housing comprising a top piece 110 and a bottom piece 130, the housing configurable to enclose the test strip assembly 120, to result in a test cell sandwich. The test strip assembly 120 comprises one sample sorbent strip 121, one reagent sorbent strip 122 and one waste sorbent pad 125. The sorbent strips 121, 122 are separated by flow separator 123 at their intersection point with test strip 124. Top piece 110 comprises sample inlet 111 positioned above a first location of sample sorbent strip 121 and reagent inlet 112 positioned above a first location of reagent sorbent strip 122. Arrows 111a and 112a show the direction of the flow of the sample and reagent, respectively, along the sorbent strips 121, 122 when introduced into the inlets and contacted with the respective sorbent strips. Observation window 119 is positioned above the test site on test strip 124 and a detectable signal would be seen from observation window 119. Bottom piece 130 comprises sample chamber 131 where sample sorbent strip 121 extends into, reagent chamber 132 where reagent sorbent strip 122 extends into and waste chamber 135 where waste sorbent pad 125 extends into. Chambers 131, 132 are separated by a dividing wall 138 extending to a partial height of the device 100. The top piece may comprise biasing means 117 to push the sample sorbent strip 121 and reagent sorbent strip 122 to the bottom of the sample and reagent chambers 131, 132 respectively (FIG. 7).

Figure 4:
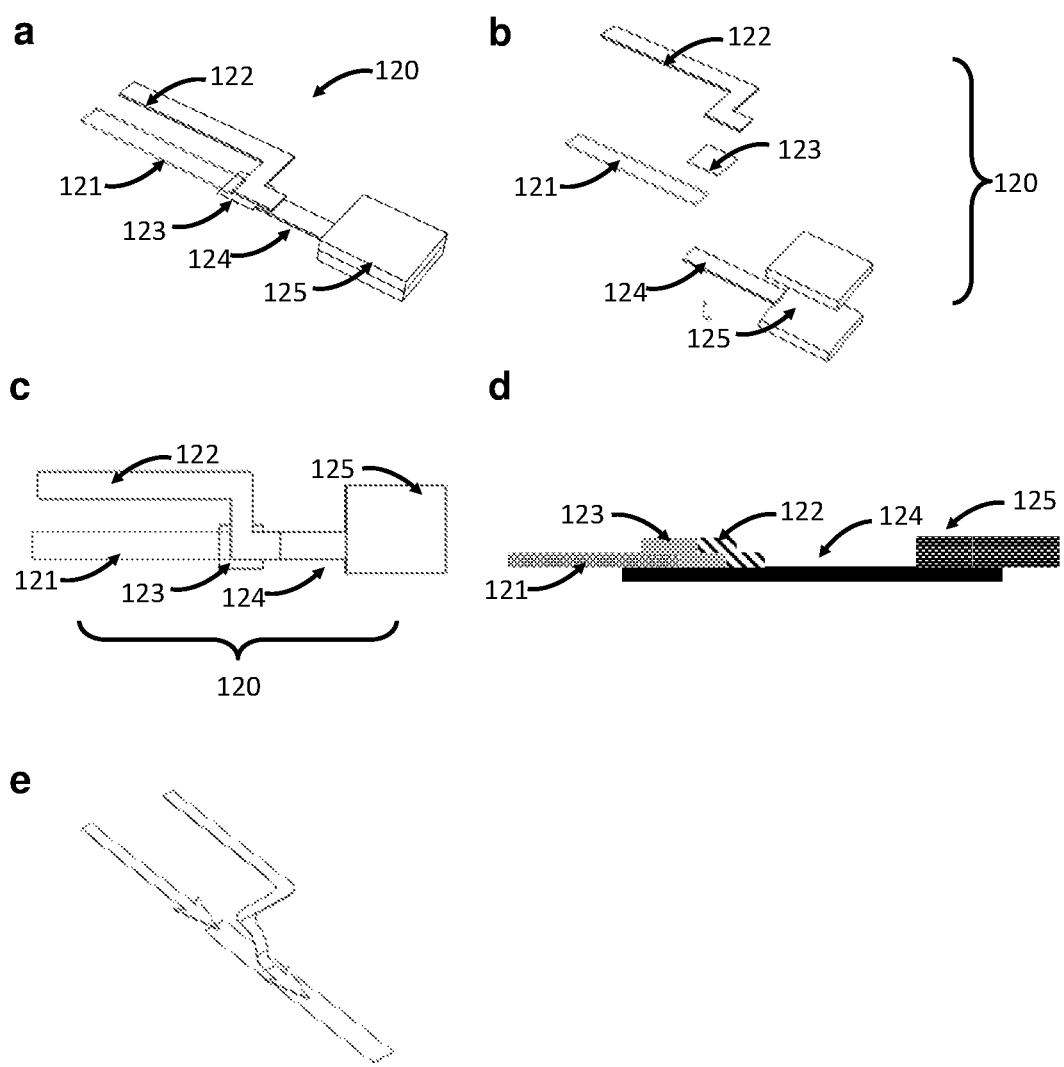

FIG. 4 shows a detailed illustration of a test strip assembly 120. Referring to FIG. 4, in use, sample sorbent strip 121 receives and guides sample liquid to the test strip 124, while reagent sorbent strip 122 receives and guides reagent liquid to the test strip 124. Test strip 124 may be a sorbent material having a high protein binding capacity. Antibodies or antigens may be immobilized on test strip 124 to form a test site where reactions take place. Waste sorbent pad 125 is provided to collect the waste samples and reagents that pass through the test strip 124. FIG. 4 shows the first locations and connecting portions of sorbent strips 121, 122 being arranged to be parallel to each other. Specifically, sample sorbent strip 121 is arranged to extend directly to test strip 124 along the same axis, while the first location and part of the connecting portion of reagent sorbent strip 122 are arranged parallel but in a different axis from strip 121. The connecting portion of reagent sorbent strip 122 is then routed or bent such that the second location of reagent sorbent strip 122 intersect with the second location of sample sorbent strip 121 and test strip 124. At the intersection, the reagent sorbent strip 122 is stacked over the sample sorbent strip 121 with flow separator 123 inserted therebetween. Flow separator 123 ensures liquids in both sample sorbent strip 121 and reagent sorbent strip 122 enter the test strip 124 without backflow. Further, flow separator 123 sets the entry point and the direction for the liquid in reagent sorbent strip 122 in such a way that liquids in sample sorbent strip 121 and reagent sorbent strip 122 migrate in the same direction when they enter the test strip 124. The flow direction is demonstrated in FIG. 4e. Without the flow separator 123, the liquid in the reagent pad 122 would enter the test strip 124 from the edge, leading to non-uniform flow in the test strip 124.

Figure 6:
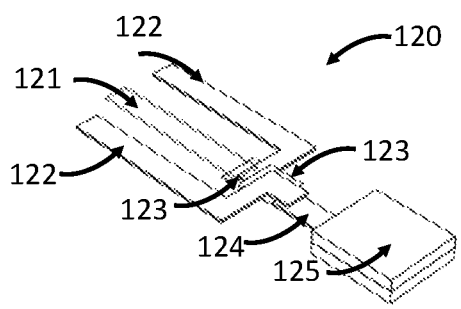
FIG. 6 is an illustration of a test strip assembly 120 comprising three sorbent strips according to an embodiment of the present invention in a) collapsed view, b) top view, and c) cross sectional view.
Figure 6:
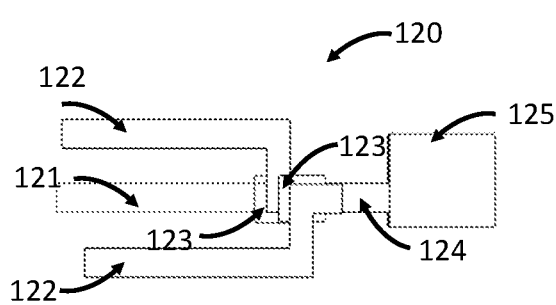
Figure 6:
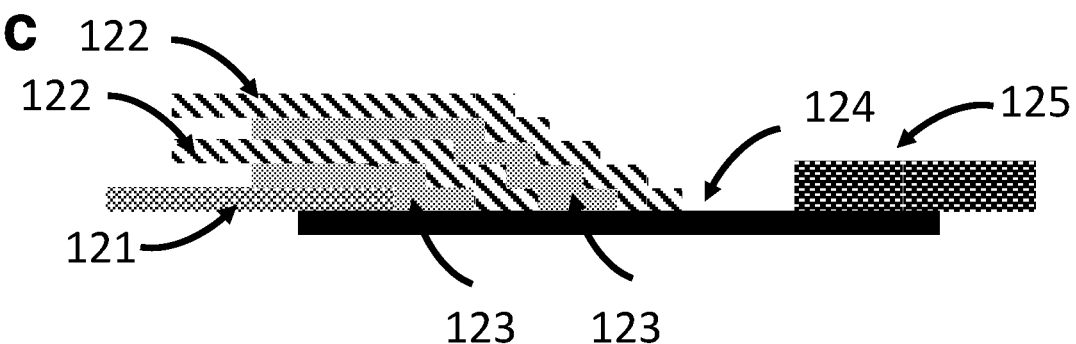

FIG. 6 shows an illustration of a test strip assembly 120 comprising one sample sorbent strip 121 and two reagent sorbent strips 122 according to an embodiment of the present invention in a) collapsed view, b) top view, and c) cross sectional view. As shown in FIG. 6, the two reagent sorbent strips 122 are stacked over sample sorbent strip 121 with two flow separators 123 inserted in between the connecting portions and second locations of the sorbent strips 121, 122. Fluids in all three sorbent strips may flow to the test strip 124 at the same time or with certain time delay as required by the assay.

The device may further comprise a flip stand configurable to tilt the device at a tilting angle chosen to allow different travel times between the respective first locations and the test site. Advantageously, the permeation of the sample and reagent from the first locations to the test site is aided by gravity. Advantageously, the device provides lateral flow assays that are rapid and yet sensitive.

The flip stand may be mounted to the device in a position that enables the device to control the flow rate of the fluids. In an example, the flip stand may be mounted to the bottom of the device. The flip stand may be mounted to a first edge of the bottom piece of the device such that the flip stand rotates about the first edge to create a tilting angle between the flip stand and device. When set to an "Open" configuration, the flip stand may position the device on an inclined surface to increase the flow rate, thereby reducing the assaying time. The flip stand may be opened to result in a tilting angle sufficient to allow the device to be supported on a second edge of the device and flip stand opposite the first edge such that the fluids flow from the sorbent strips towards the test strip. The flip stand may incline the device to result in an increased fluid flow towards the test strip. When set to a "Close" configuration, the flip stand may be arranged adjacent to the bottom piece, i.e. when the tilting angle is zero, so that the device remains compact.

Figure 2:
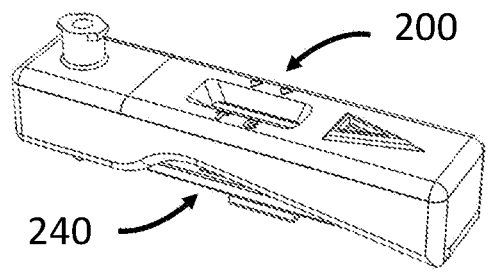
FIG. 2 is an illustration of a device 200 according to an embodiment of the present invention comprising a flip stand 240 in a) "Close" configuration and b) "Open" configuration.
Figure 2:
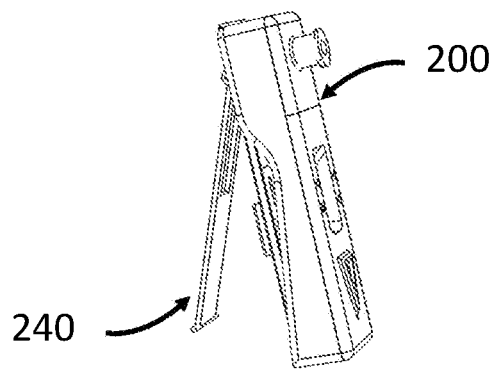

A device 200 according to an embodiment as disclosed herein is illustrated in FIG. 2. The device 200 may be oriented horizontally (FIG. 2a) or inclined at an arbitrary angle (FIG. 2b) with the assistance of a flip stand 240. As seen in FIG. 2a, the device 200 is set by default to a "Close" configuration where flip stand 240 is fitted adjacent to the bottom piece, i.e. when the tilting angle is zero. Once the sample and reagent are applied, the flip stand 240 is opened to mount the device in an "Open" or standing configuration at a desired non-zero tilting angle, as shown in FIG. 2b. By adjusting the tilting angle, the user may control the flow rate to reduce the assaying time and improve the assay performance.

In a third aspect, the present invention refers to a method of detecting the possible presence of at least one analyte in a sample using the device as disclosed herein. The method may comprise introducing the sample into the sample inlet to allow the sample sorbent strip to absorb the sample; introducing the reaction reagent into the reagent inlet to allow the reagent sorbent strip to absorb the reaction reagent; reading a signal generated on the test strip at the test site indicating the presence or absence of the at least one analyte.

The sample permeates through the sample sorbent strip by capillary action along the sample flow path to the second location. The reagent permeates through the reagent sorbent strip by capillary action along the reagent flow path to the second location. At the intersection, the test strip assembly is configured as disclosed herein to enable the sample and reagent to flow from the sorbent strips and contact the test strip in substantially the same direction. Advantageously, the reaction and detection of the presence of the analyte at the test site may be conducted substantially uniformly across substantially the entire width of the test strip. Advantageously, the disclosed method may provide a signal that is sufficiently evident and substantially uniform as seen through the observation window.

The sample and the reagent may be introduced concurrently to allow the sample and the reagent to contact the test strip at the same time, as required by the assay. Advantageously, the test strip assembly is configured as disclosed herein to enable multiple flow paths that each carries distinct samples or reagents. Advantageously, the test strip assembly is configured as disclosed herein to enable multiple flow paths to migrate concurrently and enter the test strip and test zone in the same direction. Advantageously, the flow paths enter the test strip and test zone in substantially the same direction in order to achieve uniform concurrent flow.

The sample and the reagent may be introduced shortly after each other to allow the sample flow and the reagent flow to contact the test strip at separate times, as required by the assay. The assay may require a certain time delay between introduction of the sample and the reagent and thus, the disclosed method, device and assembly may cater to a wide variety of assays due to its flexibility.

Further advantageously, the user has the flexibility to introduce the sample and reagent at any time as required by the assay. For example, the detection of certain IgM analytes may require the analytes to be captured at the test site first before reaction with detection agent particles. In another example, enzyme or silver amplification of gold nanoparticles requires introduction of liquids with time delay.

The method may further comprise immobilizing the at least one capture agent onto the test strip before assembling the device. The step of immobilizing the at least one capture agent onto the test strip may be performed as known in the art. The immobilizing step results in the formation of the test site where reactions of the assay can take place.

The capture agent may assist in the detection of the possible presence of an analyte in the sample by binding to the analyte, if present. The capture agent may be selected to be capable of binding to the analyte to be detected. The capture agent may be specific to the analyte to be detected. In examples where more than one analyte is present, the capture agent may be capable of binding to all the analytes to be detected. Alternatively, one capture agent may be capable of binding to one specific analyte to be detected. Alternatively, one capture agent may be capable of binding to one group of analytes to be detected, wherein each analyte in the group comprises a binding moiety capable of binding to the capture agent. The one or more capture agents are provided on the test site for the corresponding one or more analytes to be detected. A combination of capture agents may be provided.

In an example, the capture agent may be an antigen when the analyte is an antigen-binding molecule. In another example, the capture agent may be an antigen-binding molecule when the analyte is an antigen.

The reagent may comprise a detection agent capable of generating a signal when bound to the analyte. In this example, the reagent flow path and the sample flow path may intersect before the test site to allow for the reagent to bind to the analyte in the sample. The analyte-reagent pair may then permeate through the test strip to bind to the capture agent at the test site, thereby generating a signal indicative of the presence of the analyte. Hence, the capture agent may assist in the detection of the possible presence of an analyte in the sample by binding to the analyte-reagent pair.

The reagent may comprise a detection agent capable of generating a signal when bound to a complex formed from an analyte-capture agent pair. In this example, the sample may be introduced to the first location before the reagent is introduced and therefore may reach the test site before the reagent. The analyte in the sample may bind to the capture agent but may only generate a signal indicative of the presence of the analyte when the reagent reaches the test site and binds to the analyte-capture agent pair.

The capture agent may be selected to be capable of binding to the analyte or analyte-reagent pair to be detected. The capture agent may be specific for the analyte or analyte-reagent pair to be detected. In examples where more than one analyte or analyte-reagent pair is present, the capture agent may be capable of binding to all the analytes or analyte-reagent pairs to be detected. Alternatively, a capture agent may be provided for each analyte or analyte-reagent pair.

The reagent may comprise protein-conjugated microparticles or nanoparticles. The detection agent may comprise protein-conjugated microparticles or nanoparticles. The microparticles or nanoparticles may comprise a material suitable to conjugate detection agent thereon. The microparticles or nanoparticles may be metal, such as gold. The reagent may comprise a detection agent immobilized or dehydrated on the reagent sorbent strip and a buffer solution to dissolve or suspend or release the immobilized or dehydrated detection agent. Advantageously, the buffer may be introduced in an amount sufficient to release at least some of the dry detection agent immobilized or dehydrated on the reagent sorbent strip so that the released reagent flows to the test strip for reaction. Additional buffer may be introduced as needed when more reagent is required. Advantageously, the disclosed assembly, device and method provides for a controlled and prolonged release of reagent as required by the assay.

The reagent may comprise a buffer solution comprising a detection agent. The buffer solution may be introduced on the reagent sorbent strip and dehydrated to immobilize the detection agent on the reagent sorbent strip.

The reagent may be in liquid form and may be a suspension or solution of the detection agent.

The disclosed method may further comprise preparing the reagent sorbent strip before assembling the device. The preparation of the reagent sorbent strip may be performed as required by the assay. The preparation may comprise dehydrating the buffer to leave the detection agent immobilized on the reagent sorbent strip before assembling the device. The use of dry reagents or reagents in liquid form depends on the user and/or the requirement of the assay.

The disclosed method may further comprise pretreating the sample along the sample flow path prior to contacting the test site. The pretreatment step may comprise filtering unwanted components in the sample through the sample sorbent strip. The sample may advantageously be pre-treated in the sample sorbent strip. Advantageously, the disclosed method may not require additional pretreatment steps or equipment to pre-treat the sample.

In a fourth aspect, the present invention refers to a method of detecting the possible presence of at least one target analyte in a sample by using the device as disclosed herein. As disclosed herein, the device may be used for a variety of assays.

In an example, the target analyte may be dengue-specific immunoglobulins or hepatitis B virus-specific immunoglobulins. The capture agent may be dengue antigen or hepatitis B antigen, respectively. The detection agent may be a protein-conjugated gold nanoparticle.

Embodiments of the invention are as follows:
1. A test strip assembly for detecting the possible presence of at least one analyte in a sample, comprising:
   a test strip for immobilizing at least one capture agent and detecting the analyte, if present, at a test site on the test strip;
   a sample sorbent strip having a first location for receiving the sample and a connecting portion for connecting the first location with a second location, the connecting portion defining a sample flow path to the second location;
   a reagent sorbent strip having a first location for receiving a reaction reagent for analyte detection reaction and a connecting portion for connecting the first location with a second location, the connecting portion defining a reagent flow path to the second location;
   wherein at least a portion of the test strip, the second location of the sample sorbent strip and the second location of the reagent sorbent strip intersect with each other at an intersection,
   wherein the second location of the sample sorbent strip and the second location of the reagent sorbent strip each form at the intersection a flow path directing the sample flow path and the reagent flow path towards the test strip in substantially the same direction,
   wherein the sample sorbent strip and the reagent sorbent strip contact the test strip at the same or at separate locations.
2. The assembly of statement 1, wherein the second location of the sample sorbent strip and the second location of the reagent sorbent strip are stacked on each other at the intersection.
3. The assembly of any one of the preceding statements, further comprising a flow separator to prevent the sample flow path and the reagent flow path from mixing before reaching the test strip.
4. The assembly of statement 3, wherein the flow separator allows the sample sorbent strip and the reagent flow sorbent strip to contact the test strip across substantially the entire width of the test strip.
5. The assembly of statement 4, wherein the flow separator has the same or larger width as the sorbent strips.
6. The assembly of any one of statement 3-5, wherein the flow separator is located between the second location of the sample sorbent strip and the second location of the reagent sorbent strip to prevent the flow path at the intersection from mixing before reaching the test strip.
7. The assembly of any one of the preceding statements, further comprising more than one sample sorbent strip and/or more than one reagent sorbent strip.
8. The assembly of statement 7, wherein the second locations of the sorbent strips are stacked on each other at the intersection.
9. The assembly of any one of statements 7-8, wherein flow separators are located between the second locations of adjacent sorbent strips to prevent the flow path at the intersection from mixing before reaching the test strip.
10. The assembly of statement 9, wherein each flow separator is located between two sorbent strips at the intersection.
11. The assembly of any one of statements 3-10, wherein the flow separator is made of a material that is impermeable to the sample and the reagent.
12. The assembly of statement 11, wherein the flow separator is made of a material selected from the group consisting of glass, metal and polymer.
13. The assembly of any one of the preceding statements, wherein the first location of the sample sorbent strip and the first location of the reagent sorbent strip are arranged substantially parallel to each other.

14. The assembly of any one of the preceding statements, wherein the sample sorbent strip and the reagent sorbent strip are: (i) in the same plane as the test strip; (ii) in a plane perpendicular to the plane of the test strip; or (iii) in a plane offset to the plane of the test strip.

15. The assembly of any one of the preceding statements, wherein the sample is selected from the group consisting of blood, urine, serum, saliva and sputum.

16. The assembly of any one of the preceding statements, wherein the properties of each sorbent strip are chosen to allow different travel times between the respective first locations and the test strip.

17. The assembly of statement 16, wherein said property is selected from one or more or all of the group consisting of but not limited to: pore size, porosity, bed volume and wicking rate.

18. The assembly of any one of the preceding statements, wherein the material of each sorbent strip is selected from the group consisting of glass fiber, cellulose, cellulose acetate and a combination thereof.

19. The assembly of any one of the preceding statements, wherein the thickness and/or length of each sorbent strip is chosen to allow different travel times between the respective first locations and the test strip.

20. The assembly of any one of the preceding statements, wherein the test strip is made of a material capable of binding protein.

21. The assembly of any one of the preceding statements, wherein the test strip is a nitrocellulose membrane.

22. The assembly of any one of the preceding statements, further comprising a waste sorbent pad located downstream of the test site for collecting waste reagents and/or samples that pass through the test strip.

23. The assembly of any one of the preceding statements, wherein the at least one capture agent is immobilized at the test site.

24. The assembly of any one of the preceding statements, wherein the test site is located along the length of the test strip at a point after the sample flow and the reagent flow contact the test strip.

25. The assembly of any one of the preceding statements, wherein the reagent sorbent strip comprises a detection agent immobilized thereon.

26. A device for detecting the possible presence of at least one analyte in a sample, comprising:
the test strip assembly according to any one of the preceding statements;
a housing comprising a top piece and a bottom piece, the housing configurable to enclose the test strip assembly.

27. The device of statement 26, wherein the top piece comprises a sample inlet located above the first location of each sample sorbent strip, and a reagent inlet located above the first location of each reagent sorbent strip.

28. The device of any one of statements 26-27, wherein the bottom piece comprises a sample chamber located below the first location of each sample sorbent strip, and a reagent chamber located below the first location of each reagent sorbent strip.

29. The device of statement 28, wherein the bottom piece comprises more than one sample chamber and/or more than one reagent chamber.

30. The device of statement 28 or 29, wherein the sample chamber and the reagent chamber have volumes sufficient to prevent flooding of the test strip due to large liquid volume.

31. The device of any one of statements 26-30, wherein the bottom piece comprises a waste chamber located below the waste sorbent pad.

32. The device of any one of statements 26-31, wherein the top piece further comprises biasing means to bias the sorbent strips into their respective chambers.

33. The device of any one of statements 26-32, wherein the top piece comprises an observation window located above the test site.

34. The device of any one of statements 26-33, further comprising a flip stand configurable to tilt the device at a tilting angle chosen to allow different travel times between the respective first locations and the test site.

35. A method of detecting the possible presence of at least one analyte in a sample using the device of any one of statements 26-34, comprising:
introducing the sample into the sample inlet to allow the sample sorbent strip to absorb the sample;
introducing the reaction reagent into the reagent inlet to allow the reagent sorbent strip to absorb the reaction reagent;
reading a signal generated on the test strip at the test site indicating the presence or absence of the at least one analyte.

36. The method of statement 35, wherein the sample and the reagent are introduced concurrently or shortly after each other to allow the sample and the reagent to contact the test strip at the same or at separate times.

37. The method of any one of statements 35-36, further comprising immobilizing the at least one capture agent onto the test strip before assembling the device.

38. The method of any one of statements 35-37, wherein each capture agent is selected to be capable of binding to each analyte.

39. The method of statement 38, wherein the capture agent is an antigen or an antigen-binding molecule and the analyte is an antigen-binding molecule or an antigen, respectively.

40. The method of any one of statements 35-39, wherein the reagent comprises a detection agent capable of generating a signal when bound to the analyte or a complex formed from an analyte-capture agent pair.

41. The method of statement 40, wherein the reagent comprises protein-conjugated microparticles or nanoparticles.

42. The method of any one of statements 40-41, wherein the reagent further comprises a buffer solution to dissolve or suspend the detection agent.

43. The method of any one of statements 35-42, further comprising preparing the reagent sorbent strip before assembling the device.

44. The method of statement 43, wherein the preparation comprises dehydrating the buffer to leave the detection agent immobilized on the reagent sorbent strip before assembling the device.

45. The method of any one of statements 35-44, further comprising pretreating the sample along the sample flow path prior to contacting the test site.

46. The method of statement 45, wherein the pretreatment step comprises filtering unwanted components in the sample through the sample sorbent strip.

47. A method of detecting the possible presence of at least one target analyte in a sample by using the device of any one of statements 26-34.

48. The method of statement 47, wherein the target analyte is dengue-specific immunoglobulins or hepatitis B virus-specific immunoglobulins.

49. The method of statement 48, wherein the capture agent is dengue antigen or hepatitis B antigen, respectively.
50. The method of any one of statements 47-49, wherein the detection agent is a protein-conjugated gold nanoparticle.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Example 1

Figure 3:
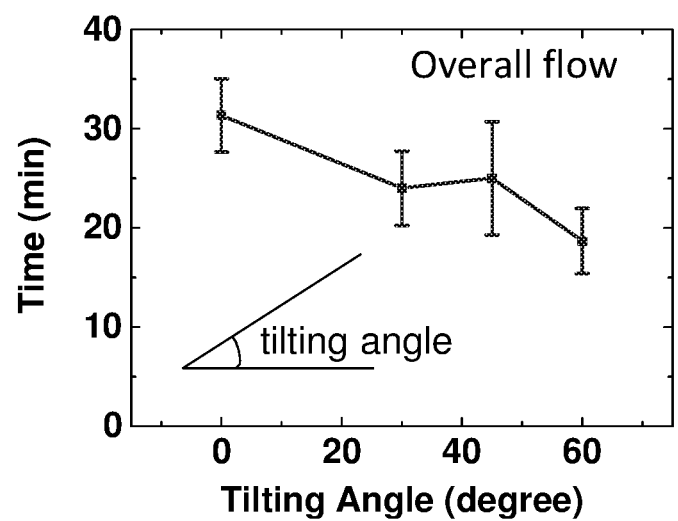
FIG. 3 is a graph showing the overall time taken for 300 µL of liquid to flow through the test strip assembly of device 200 as a function of the tilting angle in Example 1.

In this example, 300 µL of fluid was introduced into a device 200 in accordance with an embodiment of the present invention and illustrated in FIG. 2. The time taken for the fluid to flow through the length of the test strip assembly decreased with increased tilting angle, as shown in FIG. 3, thereby reducing assay reaction time by over 30% compared to when the tilting angle is zero.

Example 2

In this example, the flow characteristics of a test strip assembly in accordance with an embodiment of the present invention comprising a flow separator are compared with the flow characteristics of a test strip assembly having no flow separator.

Water was applied on the sample sorbent strip and red food dye was applied on the reagent sorbent strip. The liquid streams flowing through the sorbent strips and to the test strip was observed.

Figure 5:
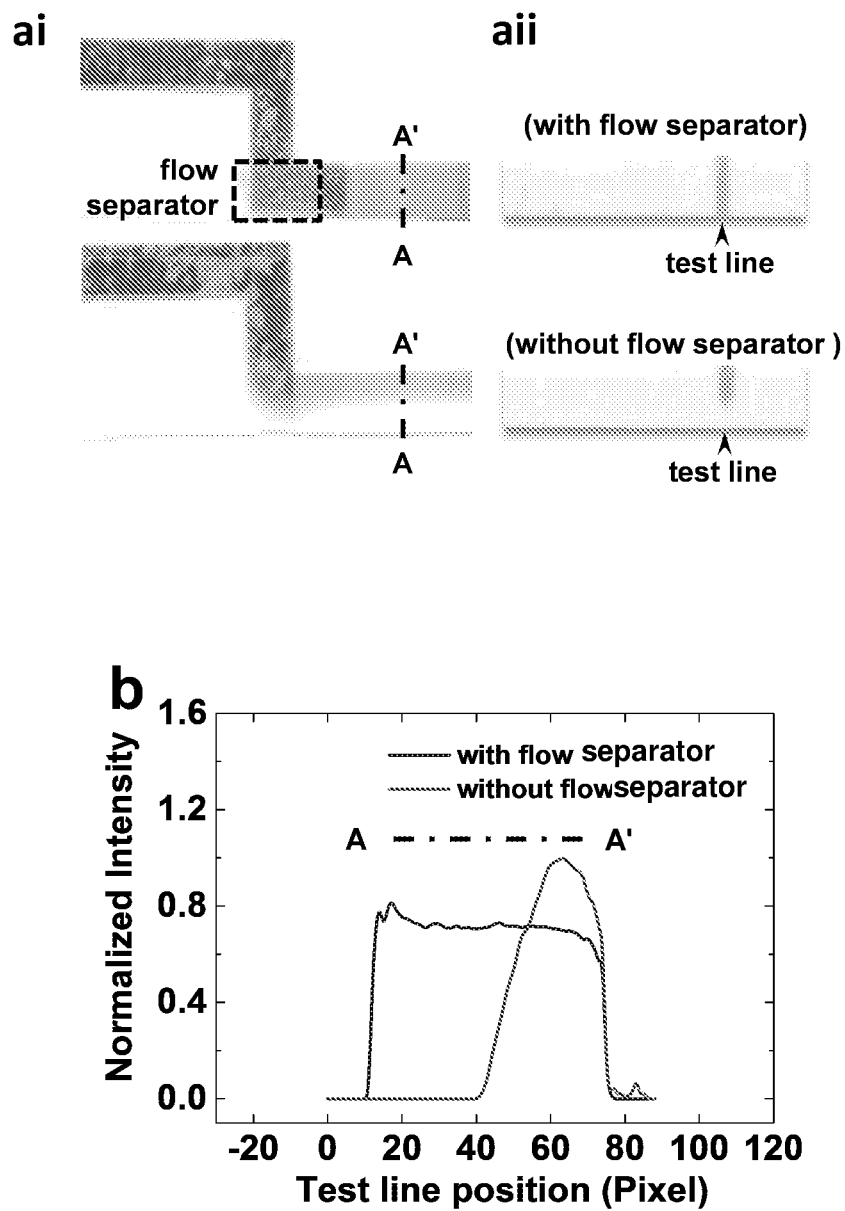
FIG. 5ai shows the passage of dye from a sorbent strip to a test strip with and without flow separator, referred to in Example 2.
FIG. 5b shows the flow profile of dye across the width of line A-A'.

It was observed that in the test strip assembly with the flow separator, the red food dye entered the test strip in the same direction as the water and encompassed the entire width of the test strip (FIG. 5*ai*). Further downstream the test strip, the dye is shown in FIG. 5*aii* at the test zone at test line A-A', where the dye was maintained across the entire width of the test strip. A clear test line at A-A' across the test strip is shown. In contrast, the flow of the liquids in the test strip assembly without the flow separator exhibited typical laminar behaviour. Specifically, the food dye flowed in a layer close to the top edge of the test strip where it entered, and pushed the water stream to the bottom edge of the test strip. FIG. 5*aii* also shows that the dye at test line A-A' did not encompass the entire width of the test strip, resulting in an uneven test line at A-A' because the dye flowed through the test strip in a layer closer to the top edge.

Example 3

Figure 8:
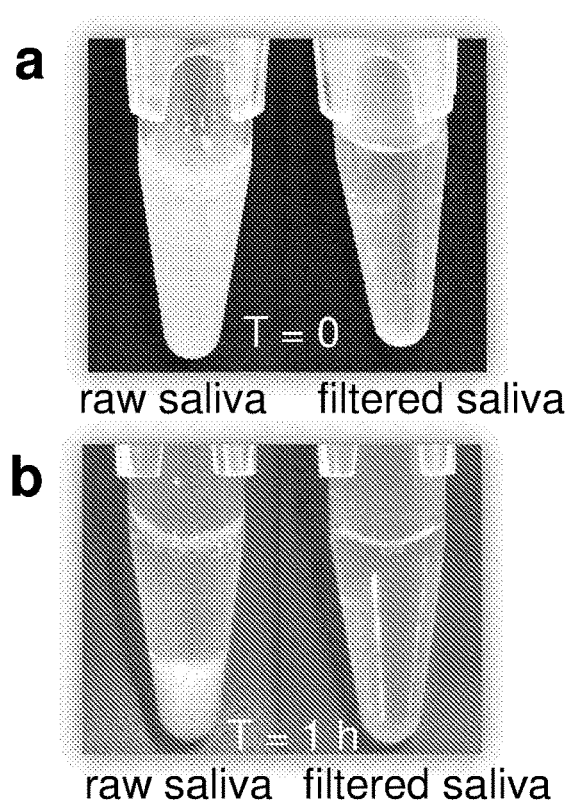
FIG. 8 shows the salivary fluid referred to in Example 3 with and without filtration a) at 0 h and b) after 1 h.

In this example, raw salivary fluids were used as the sample and were flowed through the sorbent strip to filter out any contaminants. The salivary fluids before and after filtration are compared in FIG. 8. As shown in FIG. 8*a*, the raw salivary fluid appeared turbid before filtration, but once filtered by the sorbent material of the sorbent strip, the filtered saliva appeared clear and free of solid contaminants right after filtration. Raw salivary fluid and the filtered salivary fluid were left to settle for 1 hour without disturbance and the comparison is shown in FIG. 8*b*. FIG. 8*b* evidences that solid contaminants were filtered away by the sorbent strip and the filtered saliva comprises no solid contaminants.

Example 4a

Detection of Dengue-Specific IgG in Human Saliva with Liquid Conjugate

The sample sorbent strip, reagent sorbent strip, test strip and waste absorbent pad were cut into desired sizes, and were assembled according to FIG. 1 and FIG. 4.

Dengue antigen stock was mixed with 0.1% (w/w) SDS and 100 mM of Tris (pH 7.4) at equal volume ratios. 0.5 µL of the antigen mixture was spotted onto the test strip, and dried in a vacuum chamber for 30 min. The antigen mixture formed the test site of the test strip. The nitrocellulose membrane test strip was subsequently blocked by 2% bovine serum albumin (BSA) to prevent non-specific protein adsorption. The blocked membrane was washed in 5 mM of phosphate buffer (pH 7.2), and dried in the vacuum chamber. The prepared test strips were stored in low humidity until use.

A test subject was instructed to rinse the mouth thoroughly with water and wait for at least 30 min before sample collection. To collect the saliva sample, the test subject was instructed to rinse his mouth with 2 mL of water, and spit into a sample collector. 1 µL of serum from dengue patients was then spiked into the collected saliva sample to simulate dengue-positive saliva samples. The serum was diluted 800-fold to match the IgG concentration in the saliva. The spiked saliva sample was applied to the sample sorbent strip through the sample inlet.

Figure 9:
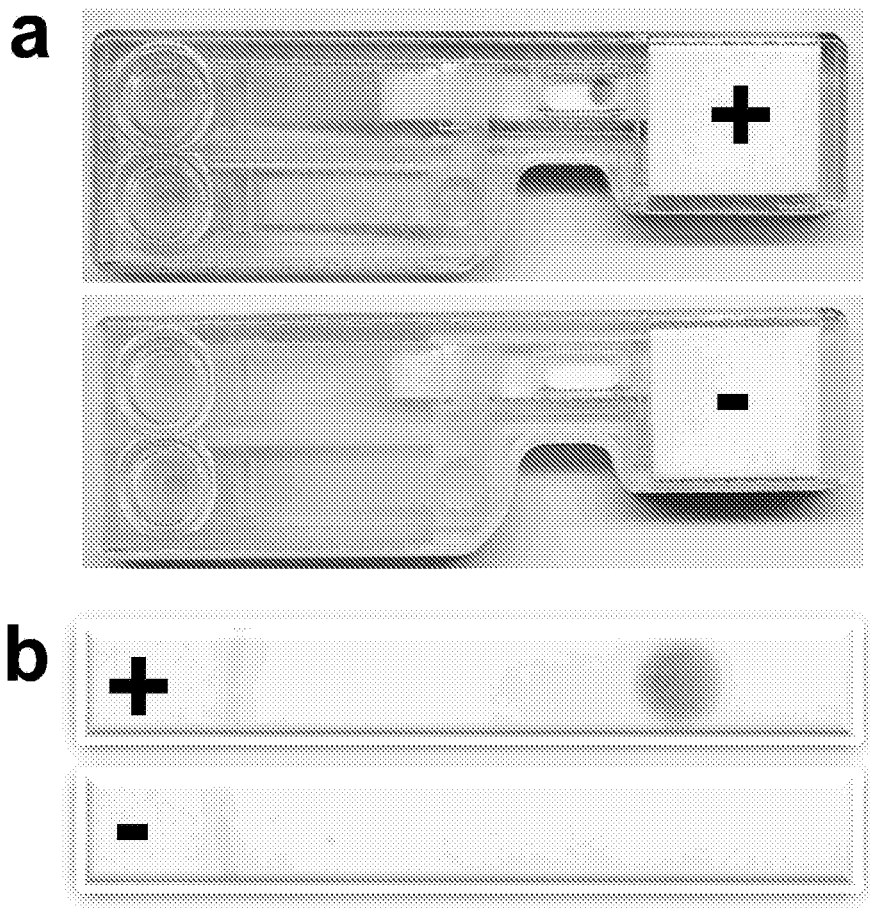
FIG. 9 shows the detection of dengue specific IgG in saliva samples in Example 4a in a) a test strip enclosed by the device, and b) the test strip alone.

300 µL of liquid conjugate containing 0.5 optical density (OD) of protein G labeled gold nanoparticles was applied to the reagent sorbent strip through the reagent inlet. Both sample and liquid conjugate were drawn to the test strip via capillary force. The signal was read after 20 min. As expected, color developed in the test site for the dengue-positive sample. The results are shown in FIG. 9, whereby FIG. 9*a* shows test strips enclosed inside the device, while FIG. 9*b* shows the test strips being removed from the device.

A negative control was also included by spiking the collected salivary fluid with serum from a healthy individual whose serum was tested negative for dengue IgG. No colorimetric signal was observed at the test site for this dengue-negative control sample. The results are also shown in FIG. 9. Both dengue-positive and dengue-negative serum samples were verified by enzyme-linked immunosorbent assay (ELISA) in 96-well plate.

Example 4b

Detection of Hepatitis B Virus (HBV) Specific IgG in Human Serum with Dry Conjugate The sample sorbent strip, reagent sorbent strip, test strip and the absorbent waste pad were cut into the desired sizes, and were assembled according to FIG. 1 and FIG. 4.

To prepare the gold nanoparticle-loaded dry reagent sorbent strip, mouse monoclonal anti-human IgG conjugated gold nanoparticles were buffered in 5% sucrose, 0.5% BSA and 2 mM of Tris (pH 7.4). 80 µL of the buffered gold nanoparticles solution were applied to the reagent sorbent strip, and allowed to dry completely under ambient condition.

Recombinant hepatitis B surface antigen (HBsAg) was buffered with 10 mM of Tris (pH 7.4). 1 µL of HBsAg at 2 mg/mL was spotted onto the test strip and dried in vacuum chamber for 30 min. The dried antigen formed the test site of the test strip. The test strip was subsequently blocked by the blocking solution (Candor Inc.) to prevent non-specific protein adsorption. The blocked membrane was washed in 5 mM of phosphate buffer (pH 7.2), and dried in the vacuum chamber.

Both HBV IgG positive serum and negative serum were separately verified by ELISA using 96-well plate. 5 µL of both serums were diluted with 95 µL of ELISA Neptune assay diluent and 100 µL of water.

Figure 10:
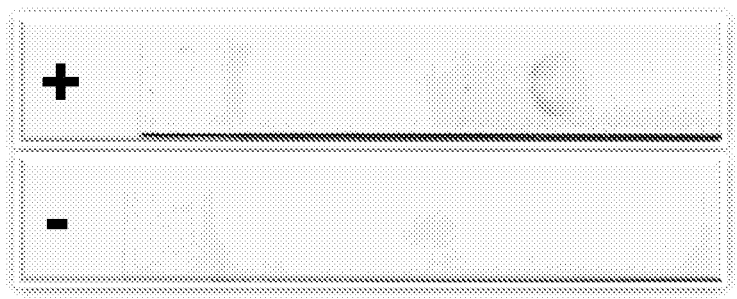
FIG. 10 shows the detection of hepatitis B virus specific IgG in saliva samples in Example 4b in the test strip according to an embodiment of the present invention.

The diluted samples were applied to the sample sorbent strip. 400 µL of running buffer containing 1×PBS, 0.2% BSA, and 0.05% Tween 20 was applied to the reagent sorbent strip. The running buffer released the dried conjugates (gold nanoparticles) from the reagent sorbent strip, and carried them to the test strip. The signal was read after 20 min. As expected, colorimetric signals only developed in the test site with HBV IgG positive serum. The results are shown in FIG. 10, evidencing that the test strip produces accurate results.

The invention claimed is:

1. A test strip assembly for detecting the possible presence of at least one analyte in a sample, comprising:
    a test strip for immobilizing at least one capture agent and detecting the analyte, if present, at a test site on the test strip;
    a sample sorbent strip having a first location for receiving the sample and a connecting portion for connecting the first location with a second location, the connecting portion defining a sample flow path to the second location;
    a reagent sorbent strip having a first location for receiving a reaction reagent for analyte detection reaction and a connecting portion for connecting the first location with a second location, the connecting portion defining a reagent flow path to the second location;
    a flow separator to prevent the sample flow path and the reagent flow path from mixing before reaching the test strip;
    wherein at least a portion of the test strip, the second location of the sample sorbent strip and the second location of the reagent sorbent strip intersect with each other at an intersection,
    wherein the second location of the sample sorbent strip and the second location of the reagent sorbent strip each form at the intersection a flow path directing the sample flow path and the reagent flow path towards the test strip in substantially the same direction,
    wherein the sample sorbent strip and the reagent sorbent strip contact the test strip at the same or at separate locations,
    wherein the second location of the sample sorbent strip and the second location of the reagent sorbent strip are stacked on each other at the intersection, and
    wherein the flow separator is located between the second location of the sample sorbent strip and the second location of the reagent sorbent strip to prevent the flow path at the intersection from mixing before reaching the test strip.

2. The assembly of claim 1, further comprising more than one sample sorbent strip and/or more than one reagent sorbent strip.

3. The assembly of claim 1, wherein the flow separator is made of a material that is impermeable to the sample and the reagent.

4. The assembly of claim 1, wherein the first location of the sample sorbent strip and the first location of the reagent sorbent strip are arranged substantially parallel to each other.

5. The assembly of claim 1, wherein the sample is selected from the group consisting of blood, urine, serum, saliva and sputum.

6. The assembly of claim 1, wherein the properties of each sorbent strip are chosen to allow different travel times between the respective first locations and the test strip.

7. The assembly of claim 1, wherein the material of each sorbent strip is selected from the group consisting of glass fiber, cellulose, cellulose acetate and a combination thereof.

8. The assembly of claim 1, wherein the test strip is made of a material capable of binding protein.

9. The assembly of claim 1, further comprising a waste sorbent pad located downstream of the test site for collecting waste reagents and/or samples that pass through the test strip.

10. The assembly of claim 1, wherein the at least one capture agent is immobilized at the test site.

11. The assembly of claim 1, wherein the reagent sorbent strip comprises a detection agent immobilized thereon.

12. A device for detecting the possible presence of at least one analyte in a sample, comprising:
    the test strip assembly according to any one of the preceding claims;
    a housing comprising a top piece and a bottom piece, the housing configurable to enclose the test strip assembly.

13. The device of claim 12, wherein the top piece comprises a sample inlet located above the first location of each sample sorbent strip, and a reagent inlet located above the first location of each reagent sorbent strip.

14. The device of claim 12, wherein the bottom piece comprises a sample chamber located below the first location of each sample sorbent strip, a reagent chamber located below the first location of each reagent sorbent strip and a waste chamber located below the waste sorbent pad.

15. The device of claim 12, wherein the top piece further comprises biasing means to bias the sorbent strips into their respective chambers.

16. The device of claim 12, wherein the top piece comprises an observation window located above the test site.

17. The device of claim 12, further comprising a flip stand configurable to tilt the device at a tilting angle chosen to allow different travel times between the respective first locations and the test site.

18. The assembly of claim 1, wherein the analyte is dengue-specific immunoglobulins or hepatitis B virus-specific immunoglobulins.

19. The assembly of claim 1, wherein the capture agent is dengue antigen or hepatitis B antigen, respectively.

20. The assembly of claim 11, wherein the detection agent is a protein-conjugated gold nanoparticle.

* * * * *